US009927355B2

(12) United States Patent
Giles et al.

(10) Patent No.: US 9,927,355 B2
(45) Date of Patent: Mar. 27, 2018

(54) FOURIER DOMAIN TERAHERTZ COHERENCE TOMOGRAPHY (TCT)

(71) Applicant: University of Massachusetts, Boston, MA (US)

(72) Inventors: Robert H. Giles, Upton, MA (US); Gargi Sharma, Revere, MA (US); Cecil S. Joseph, Lowell, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/356,722

(22) Filed: Nov. 21, 2016

(65) Prior Publication Data

US 2017/0067821 A1   Mar. 9, 2017

Related U.S. Application Data (63) Continuation of application No. PCT/US2015/030988, filed on May 15, 2015.
(Continued)

(51) Int. Cl.
*G01J 3/02* (2006.01)
*G01N 21/3581* (2014.01)
(Continued)

(52) U.S. Cl.
CPC ....... *G01N 21/3581* (2013.01); *A61B 5/0066* (2013.01); *G01B 9/0203* (2013.01);
(Continued)

(58) Field of Classification Search
CPC ... G01J 3/45; G01J 3/42; G01N 21/35; G01B 9/02
(Continued)

(56) References Cited

U.S. PATENT DOCUMENTS 5,420,681 A * 5/1995 Woodruff ............... G01J 3/02
                                                   356/326
6,388,799 B1   5/2002 Arnone et al.
(Continued)

FOREIGN PATENT DOCUMENTS

| DE | 20101046907 | * 1/2013 |
| WO | WO 2005/114295 A1 | 12/2005 |
| WO | WO 2012/131085 A1 | 10/2012 |

OTHER PUBLICATIONS

International Search Report and Written Opinion for Application No. PCT/US2015/030988 dated Aug. 25, 2015.
(Continued)

*Primary Examiner* — David Porta
*Assistant Examiner* — Meenakshi Sahu
(74) *Attorney, Agent, or Firm* — Wolf, Greenfield & Sacks, P.C.

(57) ABSTRACT

A single-shot terahertz imaging system including an interferometer and a terahertz spectrometer. The interferometer includes a beam splitter configured to receive input terahertz radiation and output first terahertz radiation and second terahertz radiation, a sample configured to reflect the first terahertz radiation, and a mirror configured to reflect the second terahertz radiation. The beam splitter is further configured to receive the reflected first terahertz radiation and the reflected second terahertz radiation, and output interfered terahertz radiation. The terahertz spectrometer is configured to measure the interfered terahertz radiation and includes a frequency dispersive element configured to receive the interfered terahertz radiation and output spatially dispersed terahertz radiation, and a terahertz radiation detector configured to determine the intensity of the spatially dispersed terahertz radiation.

25 Claims, 6 Drawing Sheets

Related U.S. Application Data (60) Provisional application No. 62/002,282, filed on May 23, 2014.

(51) Int. Cl.
*G01B 9/02* (2006.01)
*G01J 3/42* (2006.01)
*G01J 3/45* (2006.01)
*G01N 21/47* (2006.01)
*A61B 5/00* (2006.01)

(52) U.S. Cl.
CPC ..... *G01B 9/02044* (2013.01); *G01B 9/02091* (2013.01); *G01J 3/42* (2013.01); *G01J 3/45* (2013.01); *G01N 21/4795* (2013.01)

(58) Field of Classification Search
USPC .................................................. 250/339.02
See application file for complete search history.

(56) References Cited

U.S. PATENT DOCUMENTS

| | | | |
|---|---|---|---|
| 6,573,700 B2 | 6/2003 | Zhang et al. | |
| 6,665,075 B2 | 12/2003 | Mittleman et al. | |
| 6,690,001 B2 | 2/2004 | Jiang et al. | |
| 6,747,736 B2 | 6/2004 | Takahashi | |
| 6,865,014 B2 | 3/2005 | Ciesla et al. | |
| 7,693,571 B2 | 4/2010 | Arnone et al. | |
| 7,894,126 B2 | 2/2011 | Gunter et al. | |
| 8,138,477 B2 | 3/2012 | Gregory | |
| 2007/0282206 A1* | 12/2007 | Arnone | A61B 5/0059 600/473 |
| 2012/0120231 A1 | 5/2012 | Itani et al. | |
| 2013/0128267 A1* | 5/2013 | Kang | G01B 9/02074 356/326 |

OTHER PUBLICATIONS

International Preliminary Report on Patentability for Application No. PCT/US2015/030988 dated Dec. 8, 2016.

Arbab et al., Terahertz spectroscopy for the assessment of burn injuries in vivo. Journal of Biomedical Optics. Jul. 2013;18(7):077004-1-077004-7.

Chan et al., Imaging with terahertz radiation. Reports on Progress in Physics. 2007;(70):1325-79.

Kemp et al., Security applications of terahertz technology. Proc. of SPIE. 2003;(5070):44-52.

Siegel, Terahertz Technology in Biology and Medicine. IEEE MTT-S Digest. 2004:1575-8.

Wang et al., T-ray Imaging and Tomography. Journal of Biological Physics. 2003;(29):247-56.

Wu et al., Freespace electrooptic sampling of terahertz beams. Applied Physics Letters 67. Dec. 1995;(24):3523-5.

Yasuda et al., Real-time two-dimensional terahertz tomography of moving objects. Optics Communications 267. 2006:128-36.

Yasui et al., Real-time Two-dimensional Terahertz Tomography. Presentation. Tera Tech International Workshop. Osaka, Japan. 2005. 31 pages.

Yu et al., The potential of terahertz imaging for cancer diagnosis: A review of investigations to date. Quantitative Imaging in Medicine and Surgery. Mar. 2012;2(1):33-45.

Demartinis, et al., A 240 GHz Polarimetric Compact Range for Scale Model RCS Measurements. Antenna Measurements Techniques Association (ATMA), Atlanta, GA. Oct. 10-15, 2010:3-8.

Fercher et al., Measurement of Intraocular Distances by Backscattering Spectral Interferometry. Optics Communications. May 15, 1995;117:43-8.

Goyette et al., 1.56 Terahertz 2-Frames per Second Standoff Imaging. Terahertz Technology and Applications, Proc of SPIE; Jan. 2008;6893:68930J-1-11.

Goyette et al., A 1.56-THz Compact Radar Range for W-band Imagery of Scale-Model Tactical Targets. Proc of SPIE. Aug. 2000 ;4053:615-22.

Jin et al., High-Speed Terahertz Reflection Three-Dimensional Imaging for Nondestructive Evaluation. Optics Express. Nov. 5, 2012;20(23):25432-40.

Waldman et al., Submillimeter Modeling of Millimeter Radar Systems. Proc. of SPIE. Feb. 27, 1981;259:152-7.

\* cited by examiner

FIG. 6

FOURIER DOMAIN TERAHERTZ COHERENCE TOMOGRAPHY (TCT)

CROSS-REFERENCE TO RELATED APPLICATIONS

This application is a continuation of International PCT Application No. PCT/US2015/030988 filed May 15, 2015, which claims the benefit under 35 U.S.C. § 119(e) of U.S. Provisional Application No. 62/002,282, filed May 23, 2014, the contents of each of which are incorporated by reference herein in their entirety.

BACKGROUND

Optical coherence tomography (OCT) is an optical technique for acquiring three dimensional structural information about a sample. A broadband light source emits light that is split into a reference light beam and a sample light beam using a beam splitter. The sample light beam is incident upon a sample, which reflects a portion of the sample light beam back towards the beam splitter. The reference light beam is incident upon a reference mirror, which reflects the reference light beam back towards the beam splitter. The reflected sample light beam and the reflected reference light beam are then mixed at the beam splitter, if the optical path difference between the reference light beam and sample light beam is within the coherence length of the light source then it results in interference of the two beams of light. The resulting interference signal is detected by a single detector in time domain optical coherence tomography (TD-OCT) and by spectrometer in Fourier domain OCT which is another variant of OCT. Information about the structure of the sample is obtained by analyzing the interference pattern. TD-OCT requires both axial and lateral scans of the sample to obtain a three-dimensional image. The axial scan allows information about the depth profile of a sample to be obtained by adjusting the position of the reference mirror, while the lateral scan allows information about the lateral profile of the sample to be obtained by raster scanning the probe light beam or the sample itself. In frequency domain OCT the reference mirror is kept fixed and the depth information of the sample is obtained by Fourier transforming the spectrometer data which gives axial scan of the sample in a single shot. A 3D profile of the sample is then acquired by scanning the sample or the sample beam itself.

Conventional OCT techniques use light with a frequency in the near infrared and/or optical range. However, these frequencies of light have low penetration depth and high attenuation and scattering in certain materials. Terahertz (THz) radiation, on the other hand, have large penetration depth, higher transmission, and low scattering in several materials where NIR and visible radiation does not. Recently, time domain coherence tomography (TD-CT) of a sample using THz radiation was demonstrated where THz radiation were detected using conventional electo-optic (EO) sampling. In the EO sampling technique, a probe light beam of optical or infrared frequency is mixed with the THz radiation in a nonlinear material. The presence of the THz radiation in the nonlinear material at the same time as the probe light results in the rotation of the polarization of the probe light. A polarizer after the nonlinear material followed by a photodetector operating at the frequency of the probe light therefore allows the intensity of the THz radiation to be measured. A delay stage in the path of the probe light is used to scan the time delay between the probe light and the THz radiation. Making measurements at different time delay values allows the entire THz radiation waveform to be mapped in time.

SUMMARY

The inventors have recognized and appreciated that the data acquisition time for TD-CT using THz radiation can be reduced by removing both the lateral scan of the reference mirror and the time delay scan of the probe light path. Accordingly, some embodiments are directed to a single-shot terahertz imaging system, including an interferometer and a terahertz spectrometer: Fourier domain terahertz coherence tomography (TCT). The interferometer includes a beam splitter configured to receive input terahertz radiation and output first terahertz radiation and second terahertz radiation, a sample configured to reflect the first terahertz radiation, and a mirror configured to reflect the second terahertz radiation. The beam splitter is further configured to receive the reflected first terahertz radiation and the reflected second terahertz radiation, and output interfered terahertz radiation. The terahertz spectrometer is configured to measure the interfered terahertz radiation and includes a frequency dispersive element configured to receive the interfered terahertz radiation and output spatially dispersed terahertz radiation, and a terahertz radiation detector configured to determine the intensity of the spatially dispersed terahertz radiation.

Some embodiments are directed to a method of obtaining a depth profile of a sample using a single pulse of terahertz radiation. The method includes directing the single pulse of terahertz radiation into an interferometer; reflecting a reference portion of the terahertz radiation off a reference mirror; reflecting a sample portion of the terahertz radiation off the sample; interfering the reflected reference portion and the reflected sample portion to create interfered terahertz radiation; spatially dispersing the interfered terahertz radiation; detecting an intensity of the spatially dispersed interfered terahertz radiation at a plurality of locations; and analyzing the detected intensity at the plurality of locations to obtain the depth profile.

Some embodiments are directed to a single-shot terahertz imaging system, including: a terahertz radiation source configured to output broadband terahertz radiation; a sample configured to reflect the broadband terahertz radiation; and a terahertz spectrometer configured to measure the reflected terahertz radiation. The terahertz spectrometer includes a frequency dispersive element configured to receive the reflected terahertz radiation and output spatially dispersed terahertz radiation, and a terahertz radiation detector configured to determine the intensity of the spatially dispersed terahertz radiation.

Some embodiments are directed to a terahertz spectrometer, including: a frequency dispersive element configured to receive input terahertz radiation and output spatially dispersed terahertz radiation; and a terahertz radiation detector configured to determine the intensity of the spatially dispersed terahertz radiation.

The foregoing is a non-limiting summary of the invention, which is defined by the attached claims.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

The inventors have recognized and appreciated that quickly obtaining tomographic and spectroscopic data using THz radiation allows for real-time visualization of the structure of a sample, which may be changing over time. For example, the sample may be a biological sample with portions that move at a rate faster than the delay stages of the conventional imaging techniques. Thus, conventional techniques cannot adequately resolve the structure of the sample. Accordingly, some embodiments include an Fourier domain TCT imaging system that can acquire data without the need for performing a scan of a delay stage in a reference light beam path or a probe light beam path.

The inventors have also recognized and appreciated that an Fourier domain TCT imaging system may acquire sufficient data with a single pulse of THz radiation, further increasing the speed at which data may be acquired. Overall, the data acquisition time may be reduced by more than an order of magnitude.

The inventors have recognized and appreciated that using a broadband THz radiation source not only allows a sample's axial profile to be acquired in a "single shot" (e.g., a single pulse of THz radiation), but also allows the sample's spectroscopic signature to be simultaneously acquired at the same time as the axial profile without the need for additional measurements.

The inventors have also recognized and appreciated that single shot THz radiation measurement is not limited to use with tomography. For example, a sample may be illuminated with a single broadband pulse of THz radiation. The reflected THz radiation may be measured with a THz spectrometer to acquire the spectral characteristics of the sample. A measurement of the spectral characteristics of a sample may be used in one or more types of analysis. In some embodiments, a biomedical analysis of a sample is performed based on measuring the spectral characteristics of a sample. For example, cancerous tissue reflects THz radiation differently than healthy tissue. If the CW source is used for the imaging, then using the raster scan, only tomographic information can be extracted. If one uses pulsed system, then the depth information can also be obtained, but one would need to use an extra delay stage, which increases the complexity of the system and data acquisition time. Imaging using Fourier domain TCT not only allows to collect the tomographic but the depth information as well in single shot. Single shot THz radiation detection may also be used in a spectroscopy and chemical analysis. For instance THz radiations are sensitive to postburn formation of interstitial edema, and this can be used to differentiate partial-thickness burns that will naturally heal from those that will require surgical intervention. Many materials like different drugs and explosives have absorption lines in THz regime. By comparing a measured THz spectrum with predetermined absorption data stored in one or more available databases, THz spectroscopy is a noninvasive tool to identify if a powder is some harmful drug or explosive. The single shot detection of the THz pulse using Fourier domain TCT system is useful for these types of spectroscopic measurements. The information about a layered object with different layers composed of different materials, can also be obtained using Fourier domain TCT system in one single shot. Fourier domain TCT gives both spectroscopic and depth information at the same time in single shot measurement. Conventional techniques using conventional time domain system require two delay stages and multiple measurements to achieve the same results. In these conventional techniques, a first delay stage is required to obtain the spectroscopic information and a second delay stage is required to obtain the depth profile data related to the information of each layer of the sample. One needs to move the second delay stage for each layer of the object and scan the first delay stage at each depth layer to characterize the sample. In embodiments of the present application, the transmittance and/or reflectivity of a chemical sample may be measured using a single broadband THz radiation pulse. Alternatively, a spectroscopic analysis of a sample may be performed using a single broadband THz radiation pulse. The spectroscopy could be done, in some embodiments, remotely, e.g., by detecting chemicals in the atmosphere.

The inventors have recognized and appreciated that the single shot Fourier domain TCT techniques according to some embodiments have applications in security and material characterization. For example, THz radiation is useful in security applications because it passes through many common materials, such as clothing, but is lower energy than other types of radiation, such as X-ray. Accordingly, no photoionization occurs when a subject is irradiated by THz radiation. Thus, THz radiation is useful for investigating whether a person is hiding dangerous materials under their clothing. Additionally, THz radiation based Fourier domain TCT may be used to characterize a number of materials. For example, semiconductor based structures and pharmaceutical pills may be characterized with Fourier domain TCT using THz radiation.

In some embodiments, tomography with THz radiation is performed using Fourier domain (CT). In Fourier domain TCT, a broadband THz radiation pulse is used to illuminate a reference mirror and a sample. THz radiation reflected from the reference mirror and the sample is combined onto a dispersive that angularly separates the different frequency components, which form an interference pattern when detected by an image THz image sensor using a lens. If the sample consists of two or more layers, the intensity distribution along on the image sensor is a result of the interference between the signal reflected from the reference surface and the signal reflected from the two or more layers of the sample. The signal received by the image sensor is the coherent sum of the signals coming from the reference surface, the first and the second layer of the sample. Because of the presence of two or more surfaces, a modulation in the spectral intensity is introduced. The signal from each layer of the sample interferes with the reference signal and produce a modulation in the spectral intensity with frequencies proportional to the optical path difference between the reference surface and each of the corresponding reflecting layers. The Fourier transform of the intensity pattern at the camera may be analyzed to determine the frequencies of the modulation. Accordingly, the position of each of the reflecting layers within the sample with respect to the reference surface can be determined from the interference pattern. A frequency spectrum obtained after a Fourier transform of the spectrum intensity is referred to as an axial scan or depth scan. A single axial scan measurement allows the characterization of the different layers of the sample in single shot.

Figure 1:
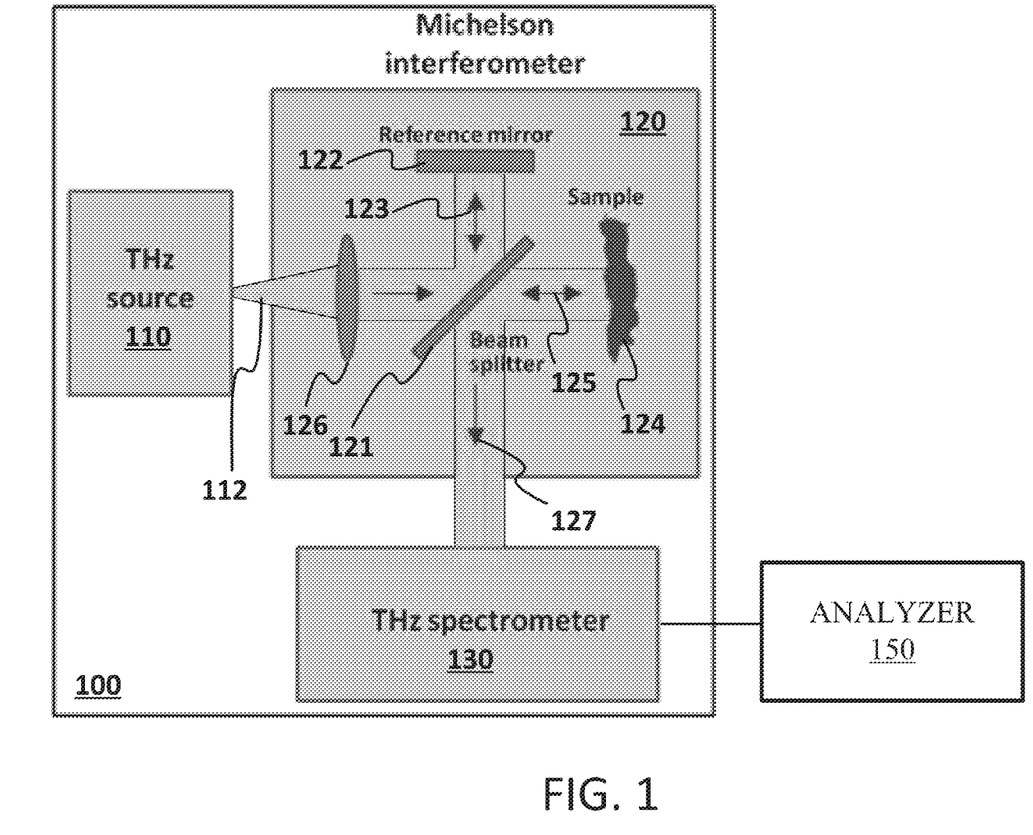
FIG. 1 is a schematic diagram of a Fourier domain TCT imaging system according to some embodiments.

FIG. 1 is a schematic diagram of a Fourier domain TCT system 100 according to some embodiments. The imaging system 100 includes three main components: a THz radiation source 110, a Michelson interferometer 120 and a THz spectrometer 130. The Fourier domain TCT imaging system 100 may also include an analyzer 150 for analyzing the spectrum obtained by the THz spectrometer.

THz radiation source 110 emits any suitable THz radiation 112, which is directed toward the Michelson interferometer 120. The Michelson interferometer receives the THz radiation 112 from the THz source 110. In some embodiments, the Michelson interferometer includes a lens 126 for collimating the THz radiation 112 received from the THz radiation source 110. In other embodiments, a collimating lens may be included in the THz radiation source 110 and the lens 126 of the Michelson interferometer may be omitted. The THz radiation 112 is incident upon a beam splitter 121, which reflects a first portion of the THz radiation 112 and transmits a second portion of the THz radiation 112. The beam splitter 121 may be any suitable beam splitter. In some embodiments, it may split the THz radiation 112 into beams of equal intensities (e.g., a "50/50 beam splitter"). However, embodiments are not so limited and any suitable splitting ratio may be used. The reflected portion of the THz radiation 112 is referred to as the reference beam 123 and the transmitted portion of the THz radiation 112 is referred to as the sample beam 125. The reference beam 123 is incident upon a reference mirror 122 that reflects the reference beam 123 back to the beam splitter 121. The sample beam 125 is incident upon a sample 124. At least a portion of the sample beam 125 is reflected back toward the beam splitter 121. The reflected reference beam 123 and the reflected sample beam 125 are reflected such that the two beams overlap on the beam splitter 121 resulting in interference. The resulting interfered THz radiation is directed towards the THz spectrometer 130, where the spectrum of the interfered THz radiation is detected.

The Fourier domain TCT system 100 may use any suitable THz radiation source 110. The THz radiation 112 may be any suitable frequency ranging, by way of example and not limitation, 0.1 THz to 10 THz. The THz radiation source 110 may be a broadband THz source that emits short pulses of THz radiation comprising a range of frequencies. In some embodiments, the THz may receive a pump beam from a pulsed laser source and generate THz radiation using the pump beam, as is known in the art.

The Fourier domain TCT system 100 may be used to characterize any suitable sample 124. By way of example and not limitation, the sample 124 may be a biological sample, a chemical sample, a semiconductor sample, or a pharmaceutical sample. The sample 124 may include a plurality of surfaces that reflect the sample beam. The location of the plurality of surfaces is part of the axial profile that may be obtained by performing measurements with the Fourier domain TCT system 100. The sample 124 may be provided by the user of the Fourier domain TCT system 100 and may not be included as part of the Fourier domain TCT system 100.

The THz spectrometer 130 detects the intensity of the interfered THz radiation 127 for a plurality of spectral ranges. Accordingly, a spectrum obtained from the THz spectrometer may be represented as a graph of the intensity of the interfered THz radiation 127 as a function of frequency. The Fourier domain TCT imaging system 100 may use any suitable THz spectrometer 130 to detect the interfered THz radiation 127 received from the Michelson interferometer 120. In some embodiments, the THz spectrometer 130 includes a frequency dispersive element that couples the frequency of incident THz radiation to a spatial degree of freedom, resulting in the direction in which the THz radiation output from the frequency dispersive element propagates being dependent on the frequency of the THz radiation. A THz radiation detector is then used to detect the dispersed THz radiation. Any suitable THz radiation detector may be used. In some embodiments, an image sensor comprising an array of charge-coupled devices (CCDs) capable of detecting THz radiation may be used. In other embodiments, the dispersed THz radiation may be used to form a beam of visible or infrared radiation with a spatial intensity profile similar to that of the dispersed THz radiation. In this way, the image sensor may include an array of CCDs capable of detecting the visible and/or infrared radiation of the probe beam, the CCD arrays in this frequency range being more sensitive than CCDs capable of detecting THz radiation.

While the analyzer 150 is illustrated as being a separate component, in some embodiments, the analyzer may be a part of the Fourier domain TCT system 100. In some embodiments, it may be included as part of the THz spectrometer 130. The analyzer 150 may be implemented in any suitable way. For example, as described in more detail below, the analyzer may be implemented using a combination of hardware and software.

The analysis performed by the analyzer 150 is described below for a particular embodiments where a sample comprising two reflecting layers, the first reflecting layer at an optical path difference of $Z_1$ from the reflecting surface of the reference mirror and the second reflecting layer at an optical path difference of $Z_2$ from the reference surface of the reference mirror. The interfered THz radiation from the Michelson interferometer is incident upon a frequency dispersive element that angularly separates the different frequency components of the interfered THz radiation. An interference pattern is formed on a linear CCD camera using a lens. At the image plane, the phase difference between the signal reflected from the reference surface and the first layer of the sample is given by $$\phi_1(k) = \phi_0 + \frac{4\pi}{\lambda} z_1, \quad \text{(Eqn. 1)}$$

where $\lambda$ is the wavelength of the THz radiation, $\varphi_0$ is the phase change introduced by reflection at the first reflecting layer and $Z_1$ is the optical path difference between the reference mirror and the first reflecting layer. Eqn. 1 can be rewritten in terms of the wave-number using the relation $k=2\pi/\lambda$, such that 1. $\varphi_1(k) = \varphi_0 + 2kz_1$ \quad (Eqn. 2), which shows a linear relationship between the phase and the wave-number. As the frequency along the k-axis is given by the rate of change of the phase with respect to the wave-number, Eqn. 2 leads to

2.

$$f_{k1} = \frac{1}{2\pi} \cdot \frac{\partial \phi_1(k)}{\partial k} = \frac{z_1}{\pi}. \quad \text{(Eqn. 3)}$$

Similarly for the second reflecting layer of the sample, the frequency of the phase is given by

3.

$$f_{k2} = \frac{1}{2\pi} \cdot \frac{\partial \phi_2(k)}{\partial k} = \frac{z_2}{\pi}. \quad \text{(Eqn. 4)}$$

The analysis may be performed in k-space as opposed to $\lambda$-space since the $f_k$ of Eqns. 3 and 4 are independent of k, whereas the equivalent frequency derived from Eqn. 1 in $\lambda$-space, would vary with $\lambda$.

The intensity distribution along k-axis on the linear CCD camera as a result of the interference between the signal reflected from the reference mirror and the signal reflected from the two reflecting layers of the sample can be expressed as 4. $I(k) = I_0(k) + 2\sqrt{I_r(k)I_1(k)} \cos(\varphi_1(k)) + 2\sqrt{I_r(k)I_2(k)} \cos(\varphi_2(k))$ (Eqn. 5), where $I_0(k)$ is a DC term, $I_r(k)$, $I_1(k)$ and $I_2(k)$ are the intensity of the signals coming from the reference surface, the first layer, and the second layer, respectively, and $\varphi_1(k)$ and $\varphi_2(k)$ are the phase difference between the signal from the reference mirror and the first reflecting layer, and the reference mirror and the second reflecting layer, respectively. Because of the presence of cosine term and the fact that the phase difference is dependent on k, a modulation in the spectrum intensity along the k-axis is introduced. In Eqn. 5, the modulation is the result of two signals with frequencies given by Eqns. 3 and 4, which are directly proportional to $Z_1$ and $Z_2$, respectively. If there were $N_i$ layers in the sample, the signal from each of these $N_i$ layers would interfere with the reference signal and produce a modulation in the spectrum intensity along the k-axis whose frequencies would be proportional to the respective optical path difference between the reference mirror and the corresponding reflecting layer.

A Fourier transform of the intensity pattern at the CCD array, after mapping each pixel location to k-space using a calibration procedure, leads to the frequencies of the modulation. Since the frequency of the modulations is proportional to the optical path difference, the position of the reflecting layers of the sample with respect to the reference surface is obtained. A frequency spectrum obtained via Fourier transform of the spectrum intensity thereby provides the axial profile (also referred to as a depth profile) of the sample without requiring a scanning of the reference mirror using a delay stage (sometimes referred to as an axial scan). In some embodiments, the optical path difference (OPD) capable of being measured may be limited by the depth range of the system, the details of which are discussed further.

In low coherence spectral domain interferometry, the available spectral bandwidth of the THz radiation source is spread over the finite number of CCD pixels. If the total bandwidth of the interfering signal acquired with Np number of pixels of the CCD camera is $\Delta k$, then the interval along the distance axis or the distance per pixel ($\Delta d$) after Fourier transform is given by $$\Delta d = \frac{1}{2} \frac{2\pi}{\Delta k}.$$

The ½ factor in this expression accounts for the doubling of the OPD after reflection. Thus the maximum OPD that can be measured as a function of the Np number of pixels of the CCD camera is

5.

$$d_{max} = \frac{1}{2} \frac{N_p}{2} \Delta d = \frac{1}{2} \frac{N_p}{2} \frac{2\pi}{\Delta k} = \frac{1}{2} \frac{N_p}{2} \frac{\lambda_0^2}{\Delta \lambda}. \quad \text{(Eqn. 6)}$$

A factor of 2 appears in the denominator of the above equation because the signal after Fourier transform (FT) is symmetric around zero OPD. For a Gaussian profiled spectrum, the depth range can be written as:

6.

$$d_{max} = \frac{1}{2} \frac{2\ln 2}{\pi} \frac{N_p}{2} \frac{\lambda_0^2}{\Delta \lambda}. \quad \text{(Eqn. 7)}$$

The THz OCT imaging system 100 is not only capable of obtaining a depth profile of a sample using a single shot, but it also records the spectrum of the THz radiation reflected from the sample. Accordingly, a spectral analysis of a sample may be performed in a single shot. The reflected spectrum from the sample allows materials within the sample to be spectroscopically identified.

Figure 2:
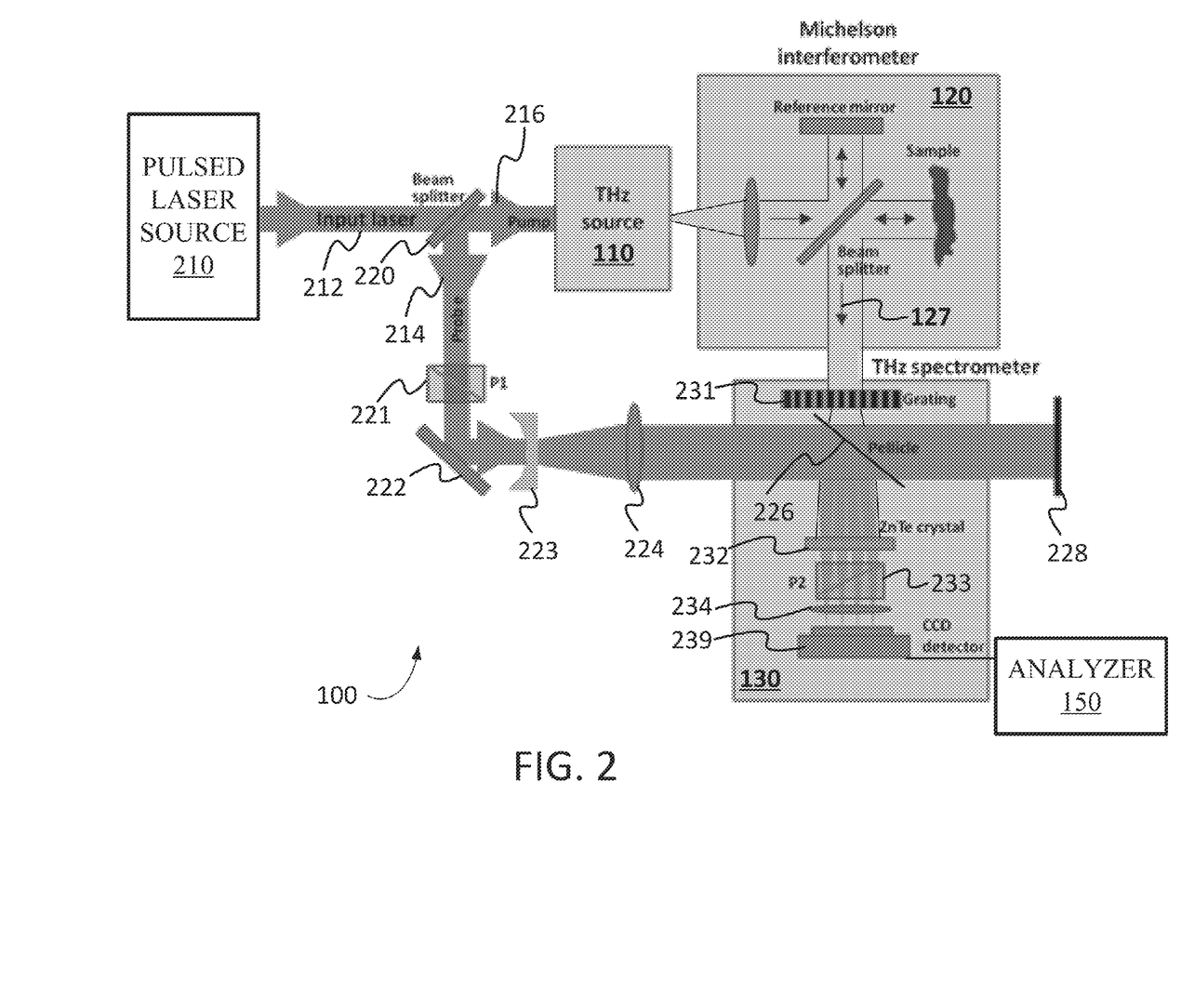
FIG. 2 is a schematic diagram of a Fourier domain TCT imaging system according to some embodiments.

FIG. 2 is a schematic diagram of a Fourier domain TCT system 100 according to some embodiments. FIG. 2 illustrates an embodiment where, rather than detecting the THz radiation from the Michelson interferometer directly, the THz radiation is detected using an electro-optic measurement that does not require the use of a delay stage in a probe beam path. Items in FIG. 2 that are similar or the same as components from FIG. 1 are labeled with the same reference number.

A pulsed laser source 210 emits input laser light 212. The pulsed laser source 210 may be any suitable broadband laser source. For example, the laser may be a titanium-sapphire ultrafast laser that emits laser pulses in the visible and/or near infrared. The input laser light 212 may be higher in frequency than THz radiation. The input laser light 212 is incident upon a beam splitter 220. A first portion of the input laser light 212, referred to as probe light 214, is directed towards the THz spectrometer 130 for use in the detection of the interfered THz radiation from the Michelson interferometer, as will be described in more detail below. A second portion of the input laser light 212, referred to as the pump light 216, is directed towards the THz source 110 where it is used to generate broadband THz pulses, as is known in the art.

The THz source 110 emits broadband THz radiation, which is directed toward the input of a Michelson interferometer 120. The details of the Michelson interferometer 120 are the same as in FIG. 1 and are not repeated here. The interfered THz radiation from the Michelson interferometer is directed to the THz spectrometer 130. The THz spectrometer 130 also receives the probe light 214 from the pulsed laser source 210, the probe light 214 having traveled through a polarizer to ensure the probe light 214 is linearly-polarized, and one or more lenses (two lenses, 223 and 224 are illustrated in FIG. 2) to make the spot size of the probe light beam 214 larger than the spot size of the line-focused THz radiation beam from the Michelson interferometer.

The interfered THz radiation 127 from the Michelson interferometer is incident upon a frequency dispersive element 231. Any suitable frequency dispersive element that angularly separates the different frequency components of the interfered THz radiation 127. In some embodiments, a prism may be used. In other embodiments, a grating may be used. The grating may be a transmissive or a reflective grating. FIG. 2 illustrates an embodiment using a transmissive THz grating.

The spatially dispersed THz radiation is mixed at a combining element 226 with the probe beam 214. In some embodiments, the combining element 226 may be a beam splitter or a polarizing beam splitter. For example, the combining element 226 may be a pellicle beam splitter. One of the two outputs of the combining element 226 is not used and may be incident upon a beam blocker 228. The second output of the combining element 226 directs the combined probe light 214 and spatially dispersed THz radiation towards a nonlinear element 232. The nonlinear element 232 may be any suitable material that exhibits the electo-optic effect, also known as Pockels effect. For example the nonlinear element 232 may be a nonlinear crystal such as Zinc telluride (ZnTe).

Because the nonlinear element 232 exhibits the Pockels effect, the spatially dispersed THz radiation creates a birefringence in the nonlinear element 232. The birefringence induced in the nonlinear element 232 is larger at locations where the intensity of the spatially dispersed THz radiation is larger. Accordingly, the polarization of the probe light is modified differently depending on the intensity of the THz radiation present at each location of the nonlinear element 232. The resulting probe light exiting the nonlinear element 232 has a polarization that varies across the spot size of the probe light beam. Embodiments are not limited to modifying the polarization of the probe light. Any suitable characteristic of the probe light may be modified by the THz radiation. For example, the intensity of the probe light may be directly modified by the presence of THz radiation.

A cross polarizer 233 is located at the output of the nonlinear element 233. The orientation of the cross polarizer is 90 degrees different from the orientation of polarizer 221. For example, if polarizer 221 is oriented to transmit horizontally polarized light, cross polarizer 233 is oriented to transmit vertically polarized light. If no THz radiation was present in the nonlinear element 232, there would be no induce birefringence and the polarization of the probe light would remain horizontally polarized. Accordingly, no probe light would be transmitted through the cross polarizer 233. However, when THz radiation creates birefringence in the nonlinear element 232, the polarization of the probe light is rotated based on the intensity of the THz radiation. Accordingly, portions of the probe light pass through the cross polarizer 233. In this way, the intensity of the spatially dispersed THz radiation is mapped onto the intensity of the probe light beam.

After the cross polarizer 233, a lens 234 is used to focus the probe light onto an image sensor 239 that detects visible and/or near infrared light. The lens may be, for example, a cylindrical lens. In some embodiments, the image sensor 239 is a CCD array detector. The recorded spectrum from the image sensor is then analyzed by the analyzer 150 as discussed above to determine the depth profile of sample 120.

Figure 3:
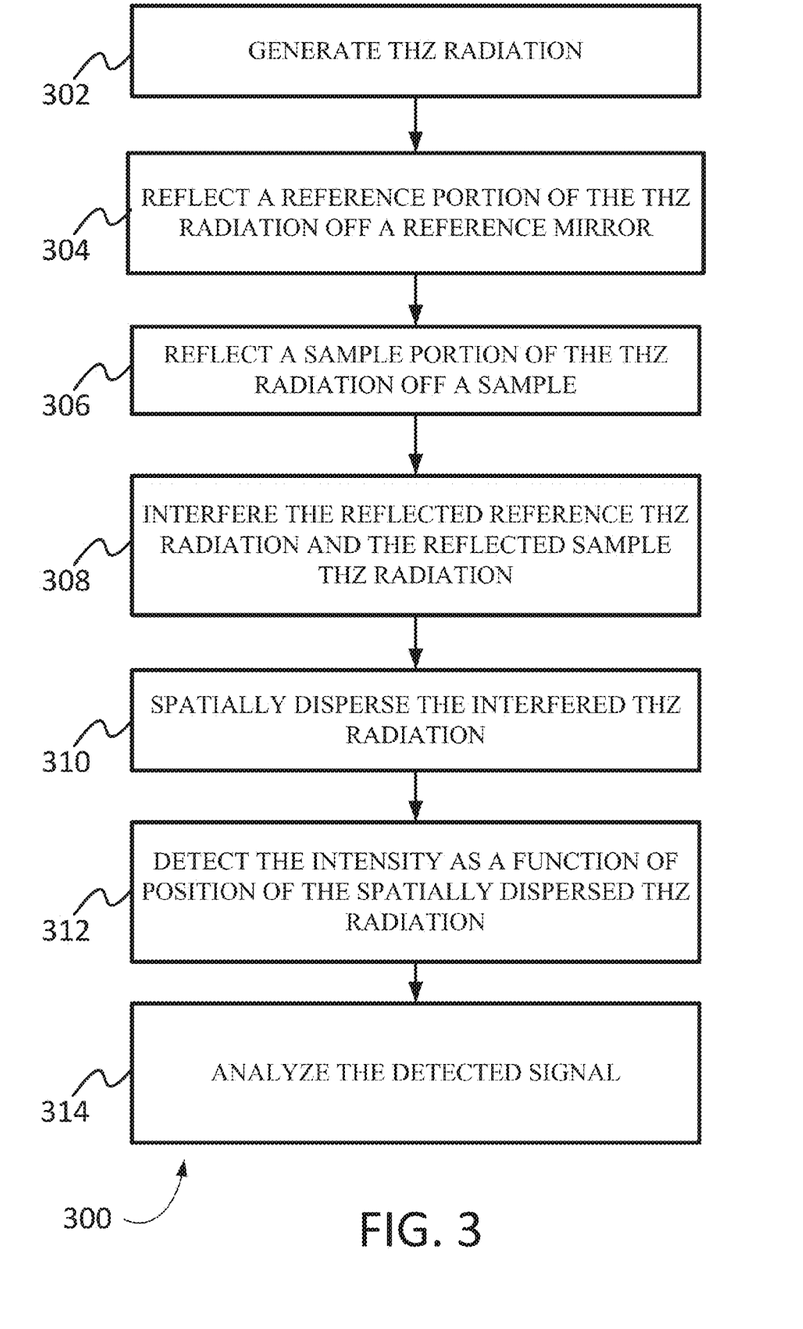
FIG. 3 is a flow chart of a method of performing THz optical coherence tomography according to some embodiments.

FIG. 3 is a flow chart of a method 300 of performing Fourier domain THz coherence tomography according to some embodiments. At act 302, THz radiation is generated by a THz radiation source. In some embodiments, the THz radiation may be a broadband pulse of THz radiation.

At act 304, a reference portion of the THz radiation is reflected off a reference mirror. At act 306, a sample portion of the THz radiation is reflected off a sample. In some embodiments, acts 304 and 306 occur at the same time. In some embodiments, acts 304 and 306 may be achieved by using a beam splitter to split the THz radiation generated at act 302 into the reference portion and the sample portion.

At act 308, the reflected reference THz radiation and the reflected sample THz radiation are interfered with one another. In some embodiments, this is accomplished by directing the reflected reference THz radiation and the reflected sample THz radiation back towards the beam splitter such that the two beams spatially overlay with one another at the beam splitter.

At act 310, the interfered THz radiation is spatially dispersed. This may be accomplished using any suitable frequency dispersive element. In some embodiments, the frequency dispersive element may be a prism. In other embodiments, the frequency dispersive element may be a grating, such as a transmissive grating or a reflective grating.

At act 312, the intensity of the spatially dispersed THz radiation is detected at a plurality of positions. In some embodiments, this may be accomplished using an image sensor comprising a plurality of pixels, wherein each pixel detects the intensity of the spatially dispersed THz radiation at a particular location. In other embodiments, the THz intensity of the dispersed THz radiation may be mapped onto the intensity of a beam of light at a different frequency, which is subsequently detected by an image sensor. This arrangement is described in more detail in connection with FIG. 4.

At act 314, the detected signal is analyzed. In some embodiments, the analysis is performed by at least one processor executing software. A method for performing the analysis is described below in connection with FIG. 5.

Figure 4:
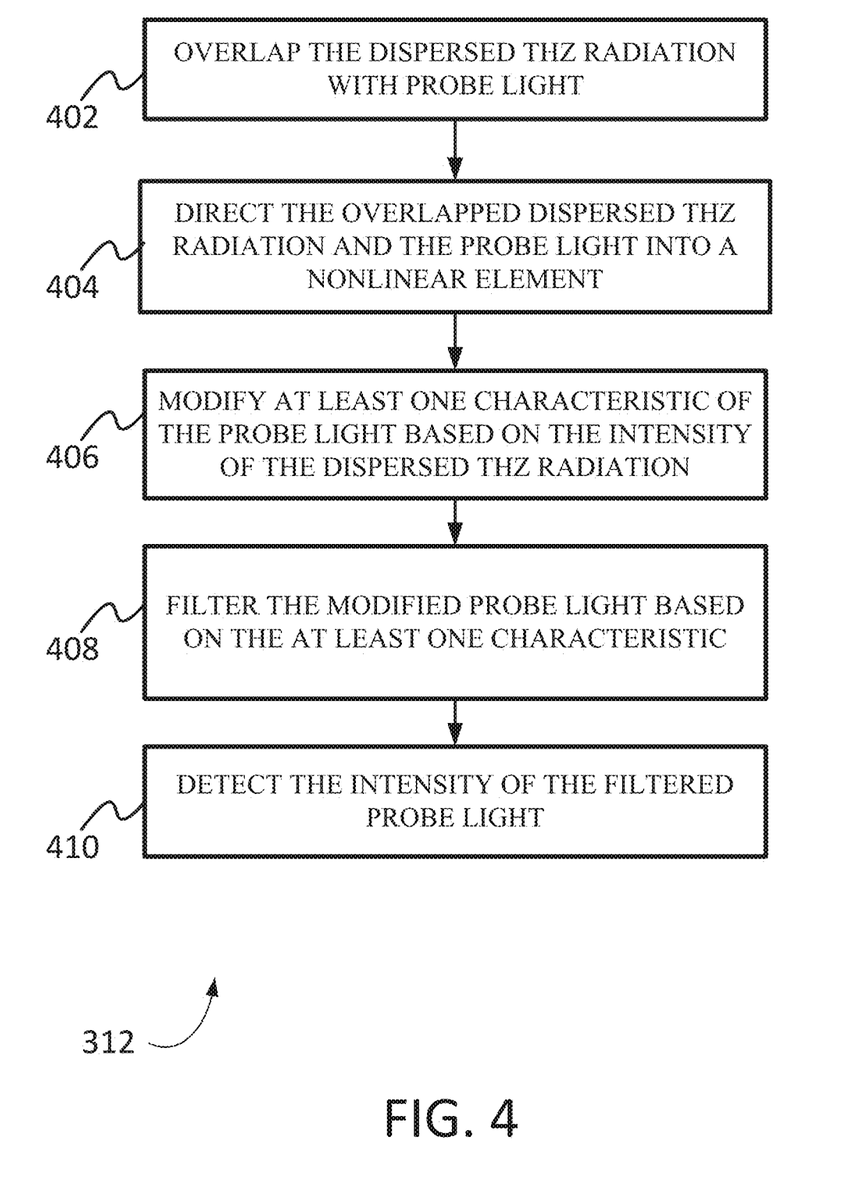
FIG. 4 is a flow chart of a method 312 of detecting dispersed THz radiation according to some embodiments.

FIG. 4 is a flow chart of a method 312 of detecting dispersed THz radiation according to some embodiments. At act 402, the dispersed THz radiation is mixed with probe light of a different frequency such that the THz radiation and the probe light overlap. In some embodiments, this may be done using a beam splitter, such as a pellicle. In some embodiments, a frequency of the probe light may be higher than the frequency of the THz radiation.

At act 404, the overlapped dispersed THz radiation and probe light are directed into a nonlinear element. Because there is spatial overlap, each portion of the dispersed THz radiation corresponds to a portion of the probe light at a corresponding position within the nonlinear element. In some embodiments, the nonlinear element comprises a material that exhibits the Pockels effect.

At act 406, at least one characteristic of the probe light is modified based on the intensity of the dispersed THz radiation. The at least one characteristic is modified by different amounts at different locations based on the intensity of the dispersed THz radiation at the corresponding location. In some embodiments, the at least one characteristic is the polarization of the probe light. The Pockels effect within the nonlinear element may create a birefringence in the nonlinear element, which results in a modification of the probe polarization at different locations within the nonlinear element.

At act 408, the modified probe light is filtered based on the at least one characteristic. In some embodiments, this may be achieved using a polarizer that is oriented to allow light that is orthogonal to a polarization state of the probe light prior to the modification of act 406.

At act 410, the intensity of the filtered probe light is detected. In some embodiments, this is achieved using an image sensor comprising an array of pixels. For example, each pixel may be a CCD device that outputs an electrical signal proportional to the intensity of the probe light incident on each pixel.

Figure 5:
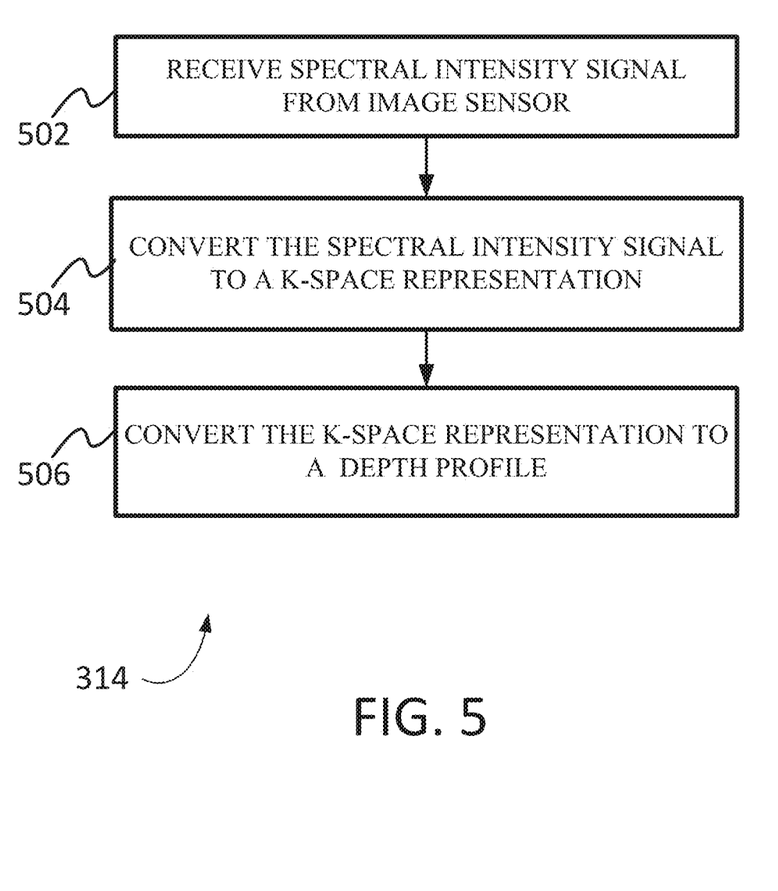
FIG. 5 is a flow chart of an analysis method 314 according to some embodiments.

FIG. 5 is a flow chart of an analysis method 314 according to some embodiments. At act 502, the spectral intensity signal is received from the image sensor. In some embodiments, the spectral intensity signal is an analog signal. In other embodiments, the spectral intensity signal is an digital signal. The spectral intensity signal provides an intensity value corresponding to each of at least a portion of the pixels of the image sensor. In some embodiments, the method 314 is performed by at least one processor. For example, an analyzer in the form of a computer system may include a processor for executing analysis software.

At act 504, the spectral intensity signal is converted to a k-space representation. In some embodiments, the spectral intensity signal received at act 502 is a set of intensities corresponding to each pixel of the image sensor. Each pixel of the image sensor maps to a particular k-value due to the frequency dispersive element used to disperse the THz radiation. Accordingly, a map that maps each pixel of the image sensor to a k-value may be used to convert the spectral intensity signal to a k-space representation.

At act 506, the k-space representation is converted into a depth profile associated with the sample. In some embodiments this may be achieved by performing a Fourier transform, such as a discrete Fourier transform, on the k-space representation. The result is a position space representation of the intensity signal, wherein the position corresponds to the depth within the sample.

Figure 6:
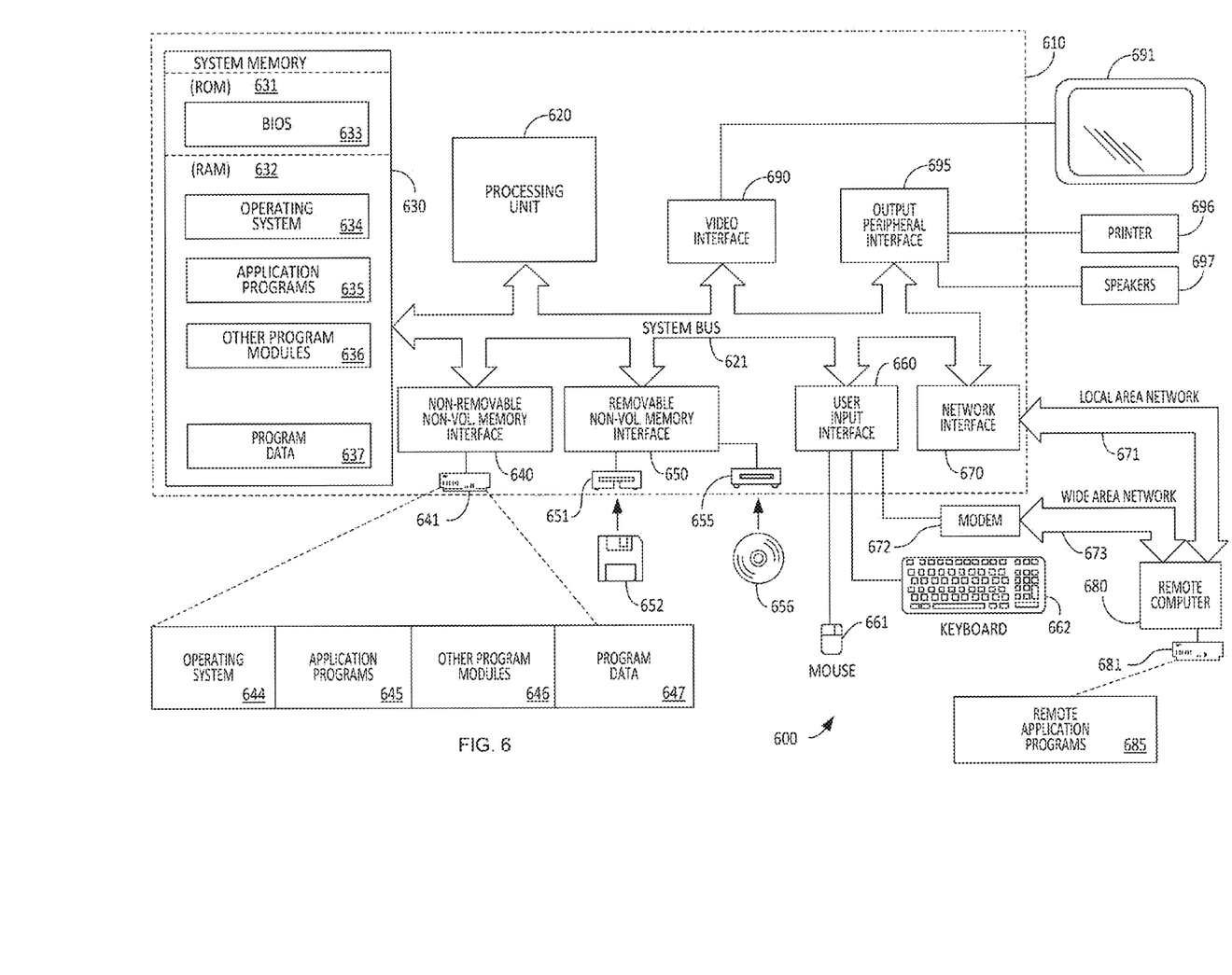
FIG. 6 is a schematic diagram of a suitable computing system environment 600 according to some embodiments.

FIG. 6 is a schematic diagram of a suitable computing system environment 600 according to some embodiments. For example, analyzer 150 may include all of or a portion of computing system environment 600. The computing system environment 600 is only one example of a suitable computing environment and is not intended to suggest any limitation as to the scope of use or functionality of embodiments herein. Neither should the computing environment 600 be interpreted as having any dependency or requirement relating to any one or combination of components illustrated in the exemplary operating environment 600.

Embodiments are operational with numerous other general purpose or special purpose computing system environments or configurations. Examples of well-known computing systems, environments, and/or configurations that may be suitable for use with some embodiments include, but are not limited to, personal computers, server computers, handheld or laptop devices, multiprocessor systems, microprocessor-based systems, set top boxes, programmable consumer electronics, network PCs, minicomputers, mainframe computers, distributed computing environments that include any of the above systems or devices, and the like.

The computing environment may execute computer-executable instructions, such as program modules. Generally, program modules include routines, programs, objects, components, data structures, etc. that perform particular tasks or implement particular abstract data types. Some embodiments may also be practiced in distributed computing environments where tasks are performed by remote processing devices that are linked through a communications network. In a distributed computing environment, program modules may be located in both local and remote computer storage media including memory storage devices.

With reference to FIG. 6, an exemplary system for implementing some embodiments includes a general purpose computing device in the form of a computer 610. Components of computer 610 may include, but are not limited to, a processing unit 620, a system memory 630, and a system bus 621 that couples various system components including the system memory to the processing unit 620. The system bus 621 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 610 typically includes a variety of computer readable media. Computer readable media can be any available media that can be accessed by computer 610 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 610. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 630 includes computer storage media in the form of volatile and/or nonvolatile memory such as read only memory (ROM) 631 and random access memory (RAM) 632. A basic input/output system 633 (BIOS), containing the basic routines that help to transfer information between elements within computer 610, such as during start-up, is typically stored in ROM 631. RAM 632 typically contains data and/or program modules that are immediately accessible to and/or presently being operated on by processing unit 620. By way of example, and not limitation, FIG. 6 illustrates operating system 634, application programs 635, other program modules 636, and program data 637.

The computer 610 may also include other removable/non-removable, volatile/nonvolatile computer storage media. By way of example only, FIG. 6 illustrates a hard disk drive 641 that reads from or writes to non-removable, nonvolatile magnetic media, a magnetic disk drive 651 that reads from or writes to a removable, nonvolatile magnetic disk 652, and an optical disk drive 655 that reads from or writes to a removable, nonvolatile optical disk 656 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 641 is typically connected to the system bus 621 through an non-removable memory interface such as interface 640, and magnetic disk drive 651 and optical disk drive 655 are typically connected to the system bus 621 by a removable memory interface, such as interface 650.

The drives and their associated computer storage media discussed above and illustrated in FIG. 6, provide storage of computer readable instructions, data structures, program modules and other data for the computer 610. In FIG. 6, for example, hard disk drive 641 is illustrated as storing operating system 644, application programs 645, other program modules 646, and program data 647. Note that these components can either be the same as or different from operating system 634, application programs 635, other program modules 636, and program data 637. Operating system 644, application programs 645, other program modules 646, and program data 647 are given different numbers here to illustrate that, at a minimum, they are different copies. A user may enter commands and information into the computer 610 through input devices such as a keyboard 662 and pointing device 661, commonly referred to as a mouse, trackball or touch pad. Other input devices (not shown) may include a microphone, joystick, game pad, satellite dish, scanner, or the like. These and other input devices are often connected to the processing unit 620 through a user input interface 660 that is coupled to the system bus, but may be connected by other interface and bus structures, such as a parallel port, game port or a universal serial bus (USB). A monitor 691 or other type of display device is also connected to the system bus 621 via an interface, such as a video interface 690. In addition to the monitor, computers may also include other peripheral output devices such as speakers 697 and printer 696, which may be connected through a output peripheral interface 695.

The computer 610 may operate in a networked environment using logical connections to one or more remote computers, such as a remote computer 680. The remote computer 680 may be a personal computer, a server, a router, a network PC, a peer device or other common network node, and typically includes many or all of the elements described above relative to the computer 610, although only a memory storage device 681 has been illustrated in FIG. 6. The logical connections depicted in FIG. 6 include a local area network (LAN) 671 and a wide area network (WAN) 673, but may also include other networks. Such networking environments are commonplace in offices, enterprise-wide computer networks, intranets and the Internet.

When used in a LAN networking environment, the computer 610 is connected to the LAN 671 through a network interface or adapter 670. When used in a WAN networking environment, the computer 610 typically includes a modem 672 or other means for establishing communications over the WAN 673, such as the Internet. The modem 672, which may be internal or external, may be connected to the system bus 621 via the user input interface 660, or other appropriate mechanism. In a networked environment, program modules depicted relative to the computer 610, or portions thereof, may be stored in the remote memory storage device. By way of example, and not limitation, FIG. 6 illustrates remote application programs 685 as residing on memory device 681. It will be appreciated that the network connections shown are exemplary and other means of establishing a communications link between the computers may be used.

Having thus described several aspects of several embodiments, it is to be appreciated that various alterations, modifications, and improvements will readily occur to those skilled in the art. For example, the inventors have also recognized and appreciated that the systems and method described above related to Fourier domain CT may be implemented without the Michelson interferometer 120. In such embodiments, THz radiation is incident upon a sample and the reflected signal is detected by the THz spectrometer 130. In such an arrangement, the depth profile of a sample may not be obtained, but the spectral information of the reflected THz radiation may be analyzed. Analysis of the spectrum of the reflected THz radiation is sufficient for some types of analysis. For example, cancerous tissue can be distinguished from healthy tissue based on the spectrum of the reflected THz radiation alone without the need for depth profile information.

Such alterations, modifications, and improvements are intended to be part of this disclosure, and are intended to be within the spirit and scope of the invention. Further, though advantages of some embodiments are indicated, it should be appreciated that not every embodiment will include every described advantage. Some embodiments may not implement any features described as advantageous herein and in some instances. Accordingly, the foregoing description and drawings are by way of example only.

Also, some methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present invention as discussed above. As used herein, the term "computer-readable storage medium" encompasses only a computer-readable medium that can be considered to be a manufacture (i.e., article of manufacture) or a machine. Alternatively or additionally, the invention may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Various aspects of the above embodiments may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which several examples have been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The invention claimed is:

1. A single-shot terahertz imaging system, comprising:
   an interferometer comprising:
      a beam splitter configured to receive input terahertz radiation and output first terahertz radiation and second terahertz radiation; and
      a mirror configured to reflect the second terahertz radiation;
      wherein the beam splitter is further configured to receive the first terahertz radiation reflected from a sample and the second terahertz radiation reflected from the mirror, and output interfered terahertz radiation;
   a terahertz spectrometer configured to measure the interfered terahertz radiation, the terahertz spectrometer comprising:
      a frequency dispersive element configured to receive the interfered terahertz radiation and output spatially dispersed terahertz radiation, the spatially dispersed terahertz radiation being output in a plurality of directions which depend on frequency; and
      a terahertz radiation detector configured to determine the intensity of the spatially dispersed terahertz radiation.

2. The single-shot terahertz imaging system of claim 1, wherein the terahertz radiation detector comprises:
   a combining element configured to spatially combine the spatially dispersed terahertz radiation and probe light from a probe light source;
   a nonlinear element configured to receive the probe light and the spatially dispersed terahertz radiation, and modify at least one characteristic of the probe light based on at least one characteristic of the spatially dispersed terahertz radiation; and
   a light detector for detecting at least a portion of the modified probe light.

3. The single-shot terahertz imaging system of claim 1, wherein the terahertz spectrometer further comprises:
   at least one analyzer configured to determine at least one characteristic of the sample based on a measurement result received from the terahertz spectrometer.

4. The single-shot terahertz imaging system of claim 3, wherein the at least one characteristic of the sample is determined without scanning a delay stage in a path of the probe light.

5. The single-shot terahertz imaging system of claim 3, wherein the at least one characteristic of the sample is determined without scanning a delay stage holding the mirror configured to reflect the second terahertz radiation.

6. The single-shot terahertz imaging system of claim 3, wherein the at least one characteristic of the sample is a depth profile.

7. The single-shot terahertz imaging system of claim 1, further comprising a terahertz radiation source configured to output the input terahertz radiation.

8. A single-shot terahertz imaging system, comprising:
   a terahertz radiation source configured to output broadband terahertz radiation and irradiate a sample that reflects the broadband terahertz radiation; and
   a terahertz spectrometer configured to measure the reflected terahertz radiation, the terahertz spectrometer comprising:
      a frequency dispersive element configured to receive the reflected terahertz radiation and output spatially dispersed terahertz radiation, the spatially dispersed terahertz radiation being output in a plurality of directions which depend on frequency; and
      a terahertz radiation detector configured to determine an intensity of the spatially dispersed terahertz radiation.

9. A terahertz spectrometer, comprising:
   a frequency dispersive element configured to receive input terahertz radiation and output spatially dispersed terahertz radiation, the spatially dispersed terahertz radiation being output in a plurality of directions which depend on frequency; and
   a terahertz radiation detector configured to determine an intensity of the spatially dispersed terahertz radiation.

10. The terahertz spectrometer of claim 9, wherein the terahertz radiation detector comprises:
   a nonlinear element configured to receive probe light and the spatially dispersed terahertz radiation, and modify at least one characteristic of the probe light based on at least one characteristic of the spatially dispersed terahertz radiation; and a light detector for detecting at least a portion of the modified probe light.

11. The terahertz spectrometer of claim 10, further comprising a combining element configured to spatially combine the spatially dispersed terahertz radiation and probe light.

12. The terahertz spectrometer of claim 11, wherein the combining element is a pellicle.

13. The terahertz spectrometer of claim 9, wherein the frequency dispersive element comprises a diffraction grating.

14. The terahertz spectrometer of claim 13, wherein the frequency dispersive element comprises a transmissive diffraction grating.

15. The terahertz spectrometer of claim 13, wherein the frequency dispersive element comprises a reflective diffraction grating.

16. The terahertz spectrometer of claim 9, wherein the frequency dispersive element comprises a prism.

17. The terahertz spectrometer of claim 10, wherein a frequency of the probe light is greater than a frequency of the terahertz radiation.

18. The terahertz spectrometer of claim 10, wherein the nonlinear element comprises an electro-optic crystal.

19. The terahertz spectrometer of claim 10, wherein the at least one characteristic of the probe light is the polarization and/or the intensity.

20. The terahertz spectrometer of claim 10, further comprising a polarizer disposed between the nonlinear element and the light detector.

21. The terahertz spectrometer of claim 9, wherein the terahertz radiation detector comprises an image sensor capable of detecting terahertz radiation.

22. The terahertz spectrometer of claim 9, wherein the terahertz spectrometer is configured to determine the spectrum of the input terahertz radiation based on a single pulse of terahertz radiation.

23. A method of obtaining a depth profile of a sample using a single pulse of terahertz radiation, comprising:

directing the single pulse of terahertz radiation into an interferometer;

reflecting a reference portion of the terahertz radiation off a reference mirror;

reflecting a sample portion of the terahertz radiation off the sample;

interfering the reflected reference portion and the reflected sample portion to create interfered terahertz radiation;

spatially dispersing the interfered terahertz radiation in a plurality of directions which depend on frequency;

detecting an intensity of the spatially dispersed interfered terahertz radiation at a plurality of locations; and analyzing the detected intensity at the plurality of locations to obtain the depth profile.

24. The method of claim 23, wherein the act of detecting comprises:

overlapping the spatially dispersed terahertz radiation with probe light;

modifying at least one characteristic of the probe light based on an intensity of the dispersed terahertz radiation;

filtering the modified probe light based on the at least one characteristic; and detecting an intensity of the filtered probe light at the plurality of locations.

25. The method of claim 23, wherein the act of analyzing the detected intensity comprises:

converting the detected intensities into a k-space representation; and converting the k-space representation into the depth profile.

* * * * *